United States Patent

Adger et al.

Patent Number: 6,066,737
Date of Patent: May 23, 2000

[54] PROCESS FOR THE PREPARATION OF OPTICALLY ENRICHED 4-ARYL-3-HYDROMETHYL SUBSTITUTED PIPERIDINES TO BE USED AS INTERMEDIATES IN THE SYNTHESIS OF PAROXETINE

[75] Inventors: Brian Michael Adger, Cambs; Gerard Andrew Potter, Leicester; Martin Edward Fox, Cambridge, all of United Kingdom

[73] Assignee: Chirotech Technology, Ltd., United Kingdom

[21] Appl. No.: 09/101,058

[22] PCT Filed: Dec. 30, 1996

[86] PCT No.: PCT/GB96/03242

§ 371 Date: Jun. 29, 1998

§ 102(e) Date: Jun. 29, 1998

[87] PCT Pub. No.: WO97/24323

PCT Pub. Date: Jul. 10, 1997

[30] Foreign Application Priority Data

Dec. 29, 1995 [GB] United Kingdom ............... 9526645

[51] Int. Cl.⁷ .................. C07D 211/22; C07D 211/60; C07D 211/20; C07D 211/40
[52] U.S. Cl. .................. 546/240; 546/245; 546/236; 546/220; 514/317
[58] Field of Search .................. 546/240, 245, 546/236, 220; 514/317

[56] References Cited

U.S. PATENT DOCUMENTS 3,912,743  10/1975  Christensen et al. ............... 546/197
5,258,517  11/1993  Zepp et al. ............... 546/240

FOREIGN PATENT DOCUMENTS 0190496  8/1986  European Pat. Off. .
0300617  1/1989  European Pat. Off. .
9100206  2/1992  WIPO .
9412816  5/1995  WIPO .
9600185  11/1996  WIPO .

OTHER PUBLICATIONS

Pierre Mangeney et al XP 000645443 J. Org. Chem. Prep and Utilization of Chiral . . . pp. 1877–1888, Aug. 4, 1994.
Pierre Mangeney et al Prep. and Utilization of Chiral Dihydrpyridine . . . J.Org. Chem. 1994 vol. 59 pp. 1877–1888, Jun. 9, 1993.

Mangeney, P., et al. (1994) Preparation and Utilization of Chiral Dihydrophyridines. Synthesis of Chiral Indoloquinolizines and Benzoquinolozines. J. Org. Chem. 59: 1877–1888.

Willcocks, K., et al. (1993) The synthesis of [$^{14}$C]–3S, 4R–4–(4–fluorophenyl)–3–(3,4–methylenedioxyphenoxymethyl) piperidine hydrochloride (BRL 29060A), and mechanistics studies using carbon–13 labelling. Journal of Labelled Compounds and Radiopharmaceuticals 33(8): 783–794.

Amat, M., Hidalgo, J., Bosch, J. (1996) Synthesis of Enantiopure 3,4–Disubstituted Piperidines. An Asymmetric Synthesis of (+)–Paroxetine. Tetrahedron: Asymmetry 7(6): 1591–1594.

Engelstoft, M., Hansen, J.B. (1996) Synthesis and 5HT Modulating Activity of Stereoisomers of 3–Phenoxymethyl–4–phenylpiperidines. Acta Chemica Scand. 50: 164–169.

*Primary Examiner*—Alan L. Rotman
*Assistant Examiner*—Rita Desai
*Attorney, Agent, or Firm*—Saliwanchik, Lloyd & Saliwanchik

[57] ABSTRACT

The subject invention pertains to optically-enriched compounds of formula (1), wherein Ar is a $C_{6-20}$ aryl group; and $R^1$ and $R^2$ are independently H, alkyl or aryl. The subject invention also pertains to method of preparing these compounds. The subject compounds can be prepared by reduction of the corresponding 1,4-dihydropyridine-3-aldehyde, e.g., using hydrogen an a catalyst. The aldehyde can be prepared by hydrolytic cleavage of an aminal obtainable by the reaction of 3-pyridinecarboxaldehyde and a chiral C-2 symmetric diamine, an then stereoselective introduction of the Ar and $COOCHR^1R^2$ groups.

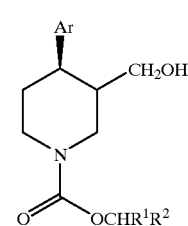

(1)

16 Claims, No Drawings

PROCESS FOR THE PREPARATION OF OPTICALLY ENRICHED 4-ARYL-3-HYDROMETHYL SUBSTITUTED PIPERIDINES TO BE USED AS INTERMEDIATES IN THE SYNTHESIS OF PAROXETINE

CROSS-REFERENCE

This application is a 371 of PCT/GB96/03242 filed Dec. 30, 1996.

FIELD OF THE INVENTION

This invention relates to optically-enriched N-acylpiperidines and their use.

BACKGROUND OF THE INVENTION

Certain chiral 3,4-disubstituted piperidines are pharmaceutically-active. The desired activity normally resides in only one of the single isomeric forms. In particular, the trans-(3S,4R)-isomer of such a compound, where the 3-substituent is 4-fluorophenyl and the 4-substituent is 3,4-methylenedioxyphenoxymethyl, i.e. paroxetine, is a potent anti-depressant drug that is widely prescribed for the treatment of depression.

Existing methods for the synthesis of single isomer paroxetine involve a resolution step. This means that the unwanted enantiomer, following resolution, is either wasted or must be converted to the desired enantiomer by an inversion process.

Willcocks et al, Journal of Labelled Compounds and Radiopharmaceuticals (1993) XXXIII(8):784–94, disclose the synthesis of $^{14}$C-labelled paroxetine. A key intermediate in this synthesis is 4-(4-fluorophenyl)-3-hydroxymethyl-1-methylpiperidine, obtained by reduction of the tetrahydropyridine. This key intermediate is converted to paroxetine by reaction with benzenesulphonyl chloride, then sesamol (with inversion), and removal of the N-methyl group. The starting material for the synthesis is a neurotoxin.

Mangeney et al, J. Org. Chem. (1994) 59:1877–85, disclose an asymmetric synthesis of 3-formyl-1,4-dihydropyridines, comprising the addition of organocopper reagents to activated 3-imidazolidinylpyridine, prepared using chiral diamines. This methodology was used for the asymmetric synthesis of indoloquinolizine and benzoquinolizine alkaloid frameworks.

SUMMARY OF THE INVENTION

This invention is based in part on the realisation that aspects of known procedures can be combined, to provide an elegant, stereoselective synthesis of paroxetine and analogues thereof. The novel synthesis provides a compound of the formula

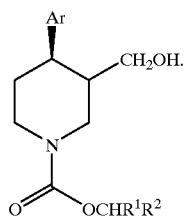

wherein Ar is a $C_{6-20}$ aryl group; and $R^1$ and $R^2$ are independently H, alkyl or aryl, e.g. of up to 10 or 20 C atoms.

This novel synthon can readily be reduced to a 1-alkylpiperidine of the type disclosed by Willcocks et al as a key intermediate en route to paroxetine. It may be prepared by reduction of the corresponding 1,4-dihydropyridine-3-aldehyde, e.g. using hydrogen and a catalyst. The aldehyde may be prepared by reduction of the dihydropyridine ring in an aminal obtainable by the reaction of 3-pyridinecarboxaldehyde and a chiral C-2 symmetric diamine, and then stereoselective 1,4-addition of the Ar and COOCHR$^1$R$^2$ groups.

DESCRIPTION OF THE INVENTION

A total synthesis of single isomer paroxetine (when Ar is 4-fluorophenyl), by means of the present invention, is shown in Scheme 1. The reactions shown in Scheme 1 are equally applicable to the preparation of the analogues that are the subject of the claims; any modifications that may be necessary will be readily apparent to one of ordinary skill in the art.

Step (i) of Scheme 1 is generally as described by Mangeney et al, supra. The aminal that is formed may be derived from a chiral C-2 symmetric diamine such as N,N'-dimethyl-1,2-cyclohexanediamine or N,N'-dimethyl-1,2-diphenylethylenediamine.

Step (ii) is the stereoselective 1,4-addition reaction. This is achieved using an appropriate organocopper reagent, and by use of a Grignard reagent using a copper catalyst. A copper (I)-catalysed coupling reagent is preferred. For example, the reagents are ArMgBr, CuBr.MeS and XCOOCHR$^1$R$^2$ where X is a reactive atom or group, e.g. a halogen atom and preferably Cl. Preferably, R$^2$ is H. More preferably, R$^1$ is also H.

Any aryl or alkyl group may include substituents that do not affect the reactions. Examples of suitable substituents will be readily apparent to those of ordinary skill in the art. For example, Ar may be halophenyl. For the COOCHR$^1$R$^2$ group, it is necessary only to convert it to alkyl, e.g. methyl, to allow the reactions described by Willcocks et al.

Step (iii) comprises hydrolytic cleavage. Steps (iv) and (v) each involve reduction reactions. The first reduction may comprise catalytic hydrogenation, e.g. using a rhodium, ruthenium, nickel, platinum or palladium catalyst, under pressure; the second reaction may comprise borohydride reduction, e.g. using NaBH$_4$.BF$_3$, in a suitable solvent. This reaction at least goes substantially without racemisation.

Steps (vi), (vii) and (viii) are essentially as described by Willcocks et al. Step (vi) shows the formation of the probable intermediate. These steps give the same product, independent of the relative configurations of the Ar and CHO/CH$_2$OH substituents in compounds of the invention.

Thus the present invention provides a practical route from 3-pyridinecarboxaldehyde to paroxetine, via certain novel intermediates shown above. In particular, the stereoselective addition is an important aspect, which unexpectedly can be conducted at a temperature higher than proposed by Mangeney et al, supra, e.g. at above −50° C. or −25° C., up to 0° C. or even ambient temperature. The reaction can be controlled by adding the third component (of the aminal, organometallic and acylating agent, usually the acylating agent as an activator for the addition reaction) to the other two, when desired.

The following Examples illustrate the invention. THF and MBTE are abbreviations for tetrahydrofuran and methyl tert-butyl ether, respectively. Example 1 describes the aminal also made by Mangeney et al, supra; that product is the starting material of Example 3.

Example 1

3-Pyridinecarboxaldehyde Aminal

3-Pyridinecarboxaldehyde (2.65 g, 28 mmol) and the diamine (S,S)-N,N'-dimethyl-1,2-diphenylethylene-1,2-diamine (6.73 g, 28 mmol) were dissolved in toluene (100 ml), stirred for 12 h, and then the solvent removed on a rotary evaporator, with the bath temperature at 70° C. The crude product thus obtained was recrystallised from pentane (8.85 g, 96%), mp 106° C.

Example 2

1,4-Addition

To a solution of the aminal from Example 1 (1.65 g, 5 mmol) in anhydrous THF (40 ml) was added methyl chloroformate (0.58 ml, 7.5 mmol). Copper (I) bromide dimethylsulfide catalyst (206 mg, 1 mmol) was then added followed by lithium bromide (174 mg, 2 mmol) to give a homogeneous yellow solution. A solution of 4-fluorophenylmagnesium bromide (1.14 M; 6.2 ml, 7.1 mmol) in THF was then added portionwise in 0.9 ml aliquots at 20 min intervals. After the addition was complete, an aqueous solution of $NH_4OH$ (1 M) was added and the product extracted with diethyl ether. The ether extracts were dried ($K_2CO_3$) and concentrated. Chromatography, on elution with cyclohexane/diethyl ether (8:1), gave the desired 1,4-dihydropyridine (1.78 g, 77%), essentially as a single enantiomer (de >95%).

Example 3

3-(1,3-Dimethyl-4(S),5(S)-diphenylimidazolidin-2-yl)-4-(4-fluorophenyl)-1,4-dihydropyridine-1-carboxylic acid methyl ester A solution of 4-bromofluorobenzene (0.95 ml, 8.6 mmol) in THF (15 ml) was added to magnesium turnings (448 mg, 2.25 mmol) under nitrogen over 10 minutes. The Grignard reaction stated immediately after the addition commenced. Additional 4-bromofluorobenzene (0.40 ml, 3.6 mmol) was added. The Grignard solution was stirred at room temperature for 1 h. A solution of 3-(1,3-dimethyl-4(S),5(S)-diphenylimidazolidin-2-yl)pyridine (2.70 g, 8.20 mmol) in THF (65 ml) was cooled to −73° C. under nitrogen. Methyl chloroformate (0.95 ml, 12.3 mmol) was added over 30 min, then copper(I) bromide dimethylsulphide complex (337 mg, 1.64 mmol) and lithium bromide (285 mmol, 3.28 mmol) were added. The suspension was allowed to warm to −50° C., and the brown/yellow solution was re-cooled to −73° C. The Grignard solution was added over 2 h. After the addition was complete, the suspension was stirred at −73° C. for 15 min, then the reaction was quenched with saturated ammonium chloride-aqueous ammonia (4:1, 55 ml). The mixture was allowed to warm to room temperature, and water (15 ml) was added. MBTE (40 ml) was added, and the aqueous phase was separated. The aqueous phase was extracted with MBTE (25 ml), and the combined organic phases were dried ($MgSO_4$) and filtered. After evaporation of the solvent, and flash chromatography on silica, eluting with heptane/MBTE (85:15) gave the dihydropyridine product as pale yellow, viscous oil (2.53 g, 67%).

Example 4

(S)-3-Formyl 4-(4-fluorophenyl)-1,4-dihydropyridine-1-carboxylic acid methyl ester Diethyl ether (210 ml) and 1M hydrochloric acid (150 ml) were added to the dihydropyridine of Example 3 (2.53 g, 5.50 mmol). The mixture was stirred at room temperature for 1.5 h, and the layers were separated. The organic layer was washed with 1M hydrochloric acid (100 ml) and saturated sodium bicarbonate solution (100 ml), and the solvent was evaporated to give the crude dihydropyridine aldehyde as a pale yellow solid (1.3 g), which was recrystallised from MBTE-heptane (1:1, 20 ml) at 0° C. to give the dihydropyridine aldehyde product as a white solid (880 mg, 61 %). The acidic aqueous layers were combined, and solid sodium hydroxide was added until the white suspension was strongly basic. The suspension was extracted with MBTE (50 ml×2) and the combined organic layers were dried ($MgSO_4$) and filtered, to give recovered 1,2-bis-N-(methylamino)-1(S),2(S)-diphenylethane as an off-white solid (1.16 g, 88%).

Example 5

(3R,4R)-4-(4-fluorophenyl)-3-hydroxymethylpiperidine-1-carboxylic acid methyl ester The dihydropyridine aldehyde of Example 4 (683 mg, 2.61 mmol) was dissolved in ethyl acetate (5 ml), and activated carbon (68 mg) was added. The suspension was stirred for 1 h at room temperature and filtered through a pad of Celite. The pad was washed with ethyl acetate (8 ml), and platinum dioxide (68 mg) was added to the solution. The suspension was hydrogenated at 13.79 kPa (200 psi) for 20 h. The suspension was filtered, and after evaporation of the solvent, flash chromatography on silica, eluting with MBTE/heptane (3:1) gave the piperidinecarbinol product as a white solid. Chiral gc analysis showed a 9:1 ratio of cis and trans piperidines. The cis piperidine was 99.3% ee., the trans >90% ee.

Example 6

(3R,4R)-4-(4-Fluorophenyl)-3-hydroxymethyl-1-methylpiperidine

Lithium aluminium hydride (87 mg, 2.30 mmol) was added to THF (2 ml) in a nitrogen-purged flask. A solution of the piperidinecarbinol of Example 5 (307 mg, 1.15 mmol) in THF (3 ml) was added dropwise. The suspension was stirred at room temperature under nitrogen for 1 h. The reaction was quenched by dropwise addition of THF-water (9:1, 1 ml), and the suspension was acidified with 2M hydrochloric acid (10 ml). The solution was extracted with MBTE (10 ml×2), and the aqueous phase was made strongly basic by adding solid sodium hydroxide. The solution was extracted with MTBE (10 ml×2), dried ($MgSO_4$), filtered, and the solvent was evaporated to give the N-methylpiperidine as a colourless, viscous oil (252 mg, 98%, 9:1 cis/trans piperidines by $^1H$, $^{13}C$ and $^{19}F$ NMR). The N-methylpiperidine was dissolved in methanol (5 ml) and conc. hydrochloric acid (4 drops) was added. The solvent was evaporated, more methanol (5 ml) was added, and the solvent was evaporated to give the N-methylpiperidine hydrochloride product as colourless needles (296 mg, 99%). This product is reported by Willcocks et al, supra, by an intermediate in the synthesis of paroxetine.

Scheme 1

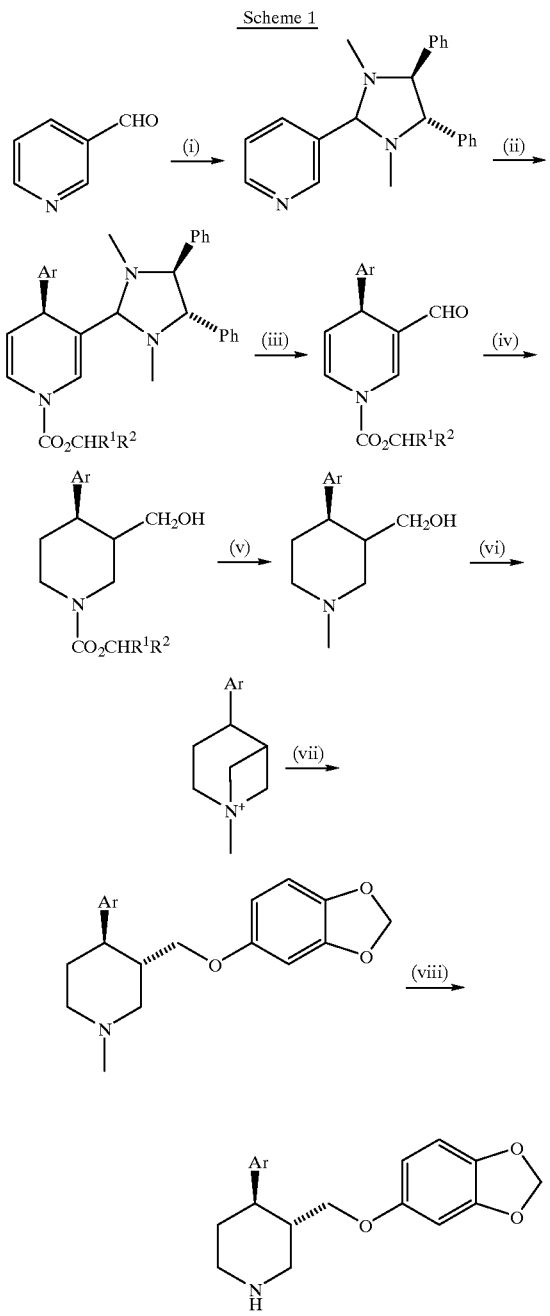

What is claimed is:

1. An optically-enriched compound of the formula

![structure]

wherein Ar is a $C_{6-20}$ aryl group; and $R^1$ and $R^2$ are independently H, alkyl or aryl.

2. The compound of claim 1, wherein $R^2$ is H.

3. The compound of claim 2, wherein $R^1$ is H.

4. The compound of claim 1, wherein the Ar and $CH_2OH$ groups are cis.

5. The compound of claim 1, in at least 80% enantiomeric excess.

6. The compound of claim 1, wherein Ar is halophenyl.

7. The compound of claim 6, wherein Ar is 4-fluorophenyl.

8. The process for preparing a compound of claim 1, which comprises reduction of the corresponding 1,4-dihydropyridine-3-aldehyde.

9. The process according to claim 8, which comprises preparing the aldehyde by hydrolytic cleavage of an aminal obtainable by the reaction of 3-pyridinecarboxaldehyde and a chiral C-2 symmetric diamine, and then introduction of the Ar and $COOCHR^1R^2$ groups, the Ar group being introduced stereoselectively.

10. The process according to claim 9, wherein the diamine is N,N'-dimethyl-1,2-diphenylethylene-1,2-diamine.

11. The process according to claim 9, wherein the introduction of the Ar group is catalysed by copper (I).

12. A method for the preparation of an anti-depressant agent from the compound of claim 1, said method comprising reducing the $COOCHR^1R^2$ group to methyl using a reducing agent, and coupling a further group through the $CH_2OH$ group.

13. A method for the preparation of paroxetine from the compound of claim 7, said method comprising reducing the $COOCHR^1R^2$ group to methyl using a reducing agent, and coupling a further group through the $CH_2OH$ group.

14. The process according to claim 8, wherein said reduction is accomplished using hydrogen and a catalyst.

15. The process according to claim 8, wherein in the compound of claim 1 Ar is halophenyl.

16. The process according to claim 8, wherein in the compound of claim 1 Ar is 4-fluorophenyl.

* * * * *